(12) United States Patent
Kimbrough et al.

(10) Patent No.: US 6,584,995 B2
(45) Date of Patent: Jul. 1, 2003

(54) HVAC ENVIRO-CLEAN VALVE

(76) Inventors: Atwood M. Kimbrough, P.O. Box 1081, Pace, FL (US) 32571; Carl Brian Kimbrough, 7066 Milton Courts, Milton, FL (US) 32583

(*) Notice: Subject to any disclaimer, the term of this patent is extended or adjusted under 35 U.S.C. 154(b) by 156 days.

(21) Appl. No.: 09/897,557

(22) Filed: Jul. 3, 2001

(65) Prior Publication Data

US 2003/0010381 A1 Jan. 16, 2003

(51) Int. Cl.[7] .......................... B08B 9/027; F21D 21/14; F28G 9/00; F16K 51/00
(52) U.S. Cl. ...................... 137/240; 62/303; 134/102.2; 134/166 C; 134/171; 137/112; 137/209; 141/89
(58) Field of Search ............................ 137/15.04, 15.05, 137/112, 114, 209, 240, 527; 62/303; 134/99.2, 102.2, 166 C, 166 R, 169 C, 171; 141/85, 89; 222/148

(56) References Cited

U.S. PATENT DOCUMENTS

| | | | | |
|---|---|---|---|---|
| 3,550,612 A | * | 12/1970 | Maxon | 137/112 |
| 4,230,174 A | * | 10/1980 | Eubank | 137/112 |
| 4,246,926 A | * | 1/1981 | Morello | 137/209 |
| 4,915,133 A | * | 4/1990 | Harrison | 137/625.47 |
| 4,998,412 A | * | 3/1991 | Bell | 62/303 |
| 5,085,244 A | * | 2/1992 | Funk | 137/240 |
| 5,664,423 A | * | 9/1997 | Akazawa | 62/303 |
| 5,737,937 A | * | 4/1998 | Akazawa | 62/303 |
| 5,964,238 A | * | 10/1999 | Junkin | 137/240 |

* cited by examiner

Primary Examiner—George L. Walton

(57) ABSTRACT

Currently, there are no products available which allow a user to treat microbial and bacterial growth inside a HVAC condensate drain line or clear a clogged line without cutting into the drain line. Our valve is an in-line condensate drain line valve that can be installed easily, quickly and economically, either during new construction or onto existing HVAC systems. The HVAC user can add household bleach to the condensate line, which inhibits microbial and bacterial growth without cutting into or disassembling the drain line. The design of our valve allows the user to perform safe routine maintenance to the HVAC drainage system without having to resort to expensive and repetitive service call repairs over the lifetime of the HVAC system. The valve is further designed to prevent undesirable reverse airflows into the HVAC system and home or building, caused by a dry water trap in the condensate drain. The prevention of reverse airflows and reduction of microbial and bacterial growth will have a positive impact of Indoor Air Quality.

3 Claims, 7 Drawing Sheets

NORMAL CONDENSATE FLOW: through Enviro-Clean Valve

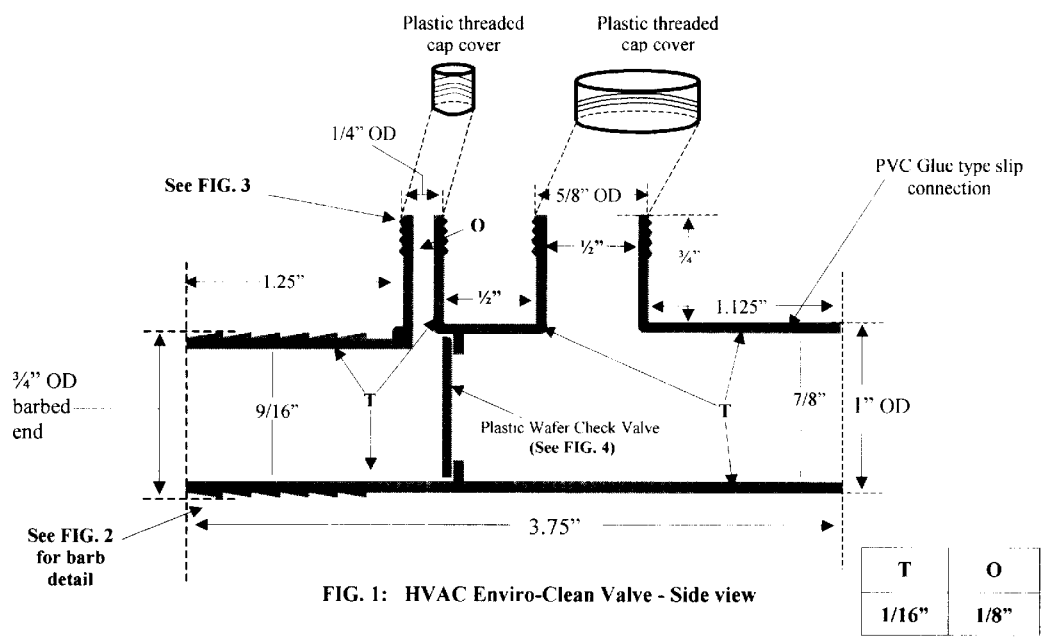
FIG. 1: HVAC Enviro-Clean Valve - Side view
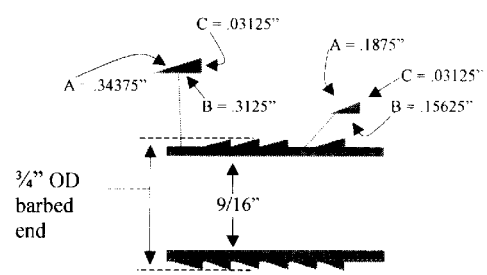
FIG. 2: Barb detail
(Barb measurements may vary)
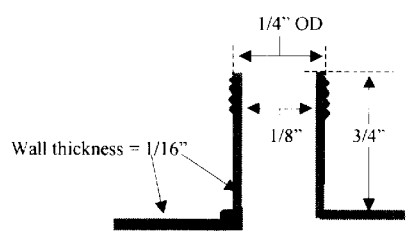
FIG 3: Air Inlet Detail

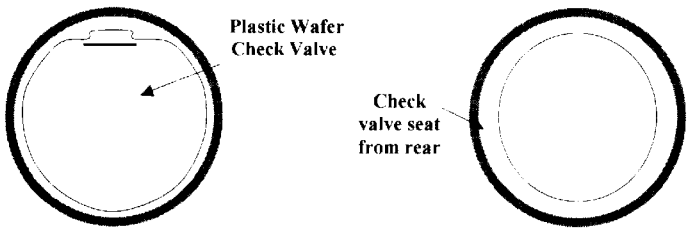
FIG. 4: Cross sectional view at Check Valve
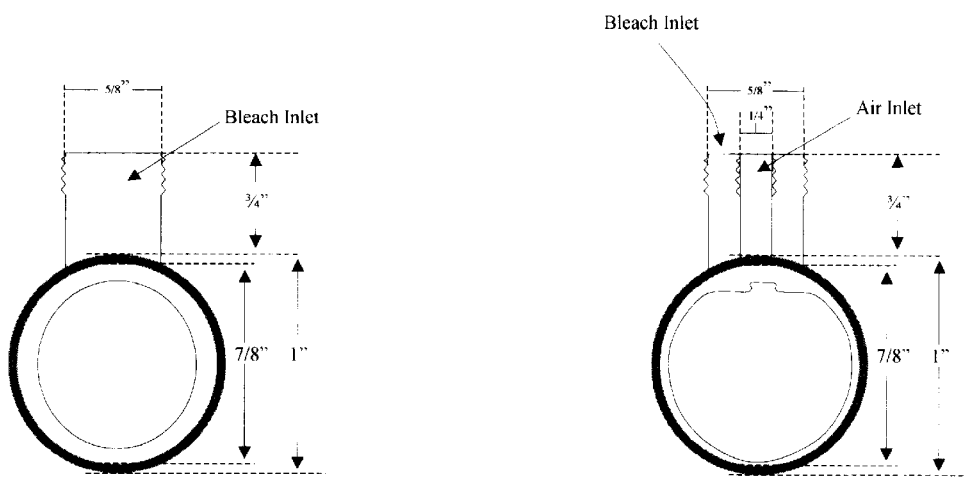
FIG 5: Cross Sectional view as seen from slip connection end
FIG. 6: Cross Sectional view as seen from barbed connection end

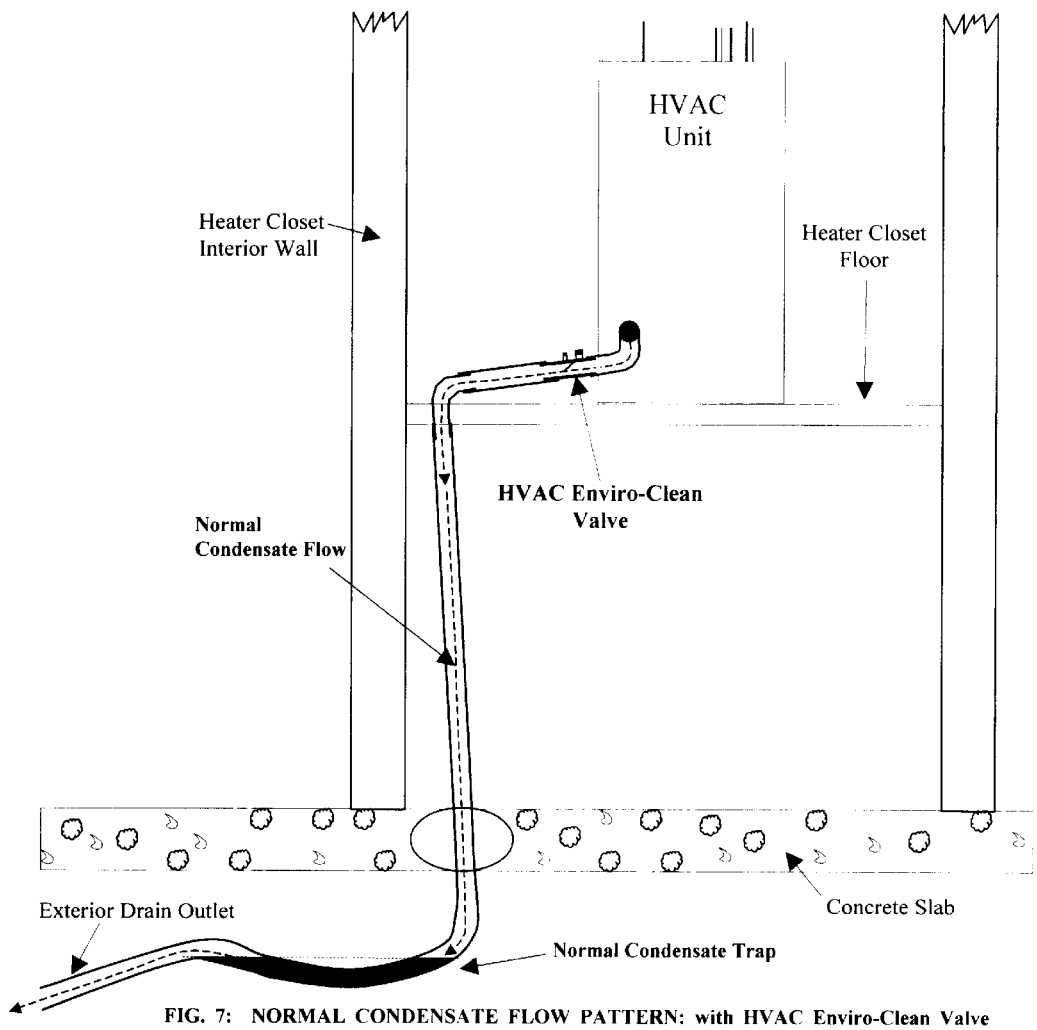
FIG. 7: NORMAL CONDENSATE FLOW PATTERN: with HVAC Enviro-Clean Valve installed.
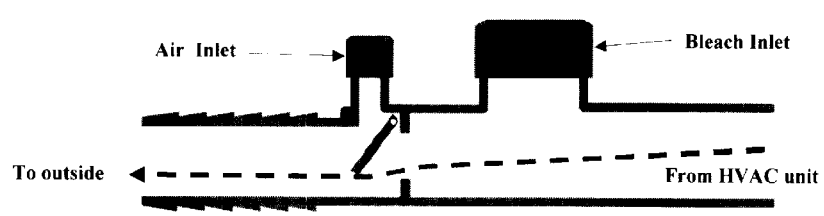
FIG. 8: NORMAL CONDENSATE FLOW: through Enviro-Clean Valve

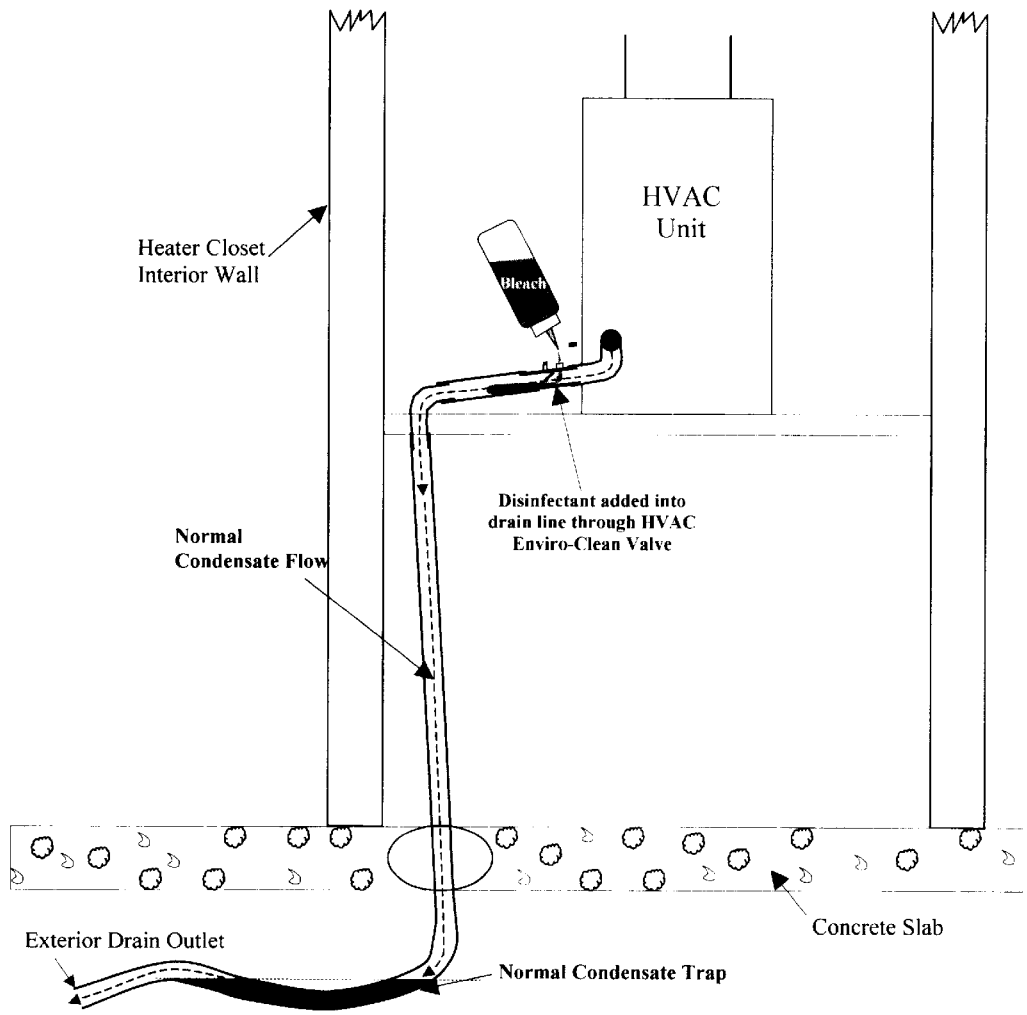
FIG. 9: INTRODUCTION OF DISINFECTANT: Disinfectant input into condensate drain line through HVAC Enviro-Clean Valve.
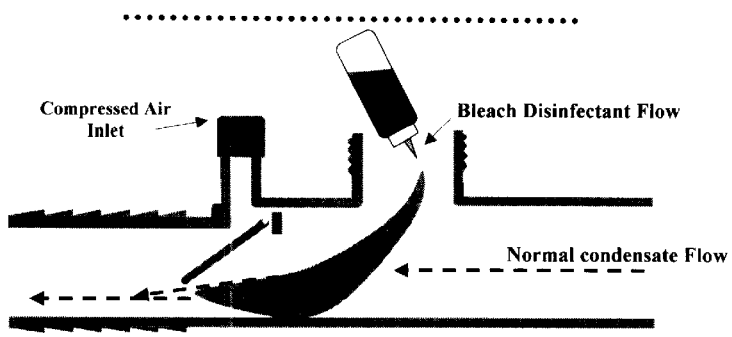
FIG. 10: DISINFECTANT FLOW PATTERN: Disinfectant flow through Enviro-Clean valve toward condensate trap.

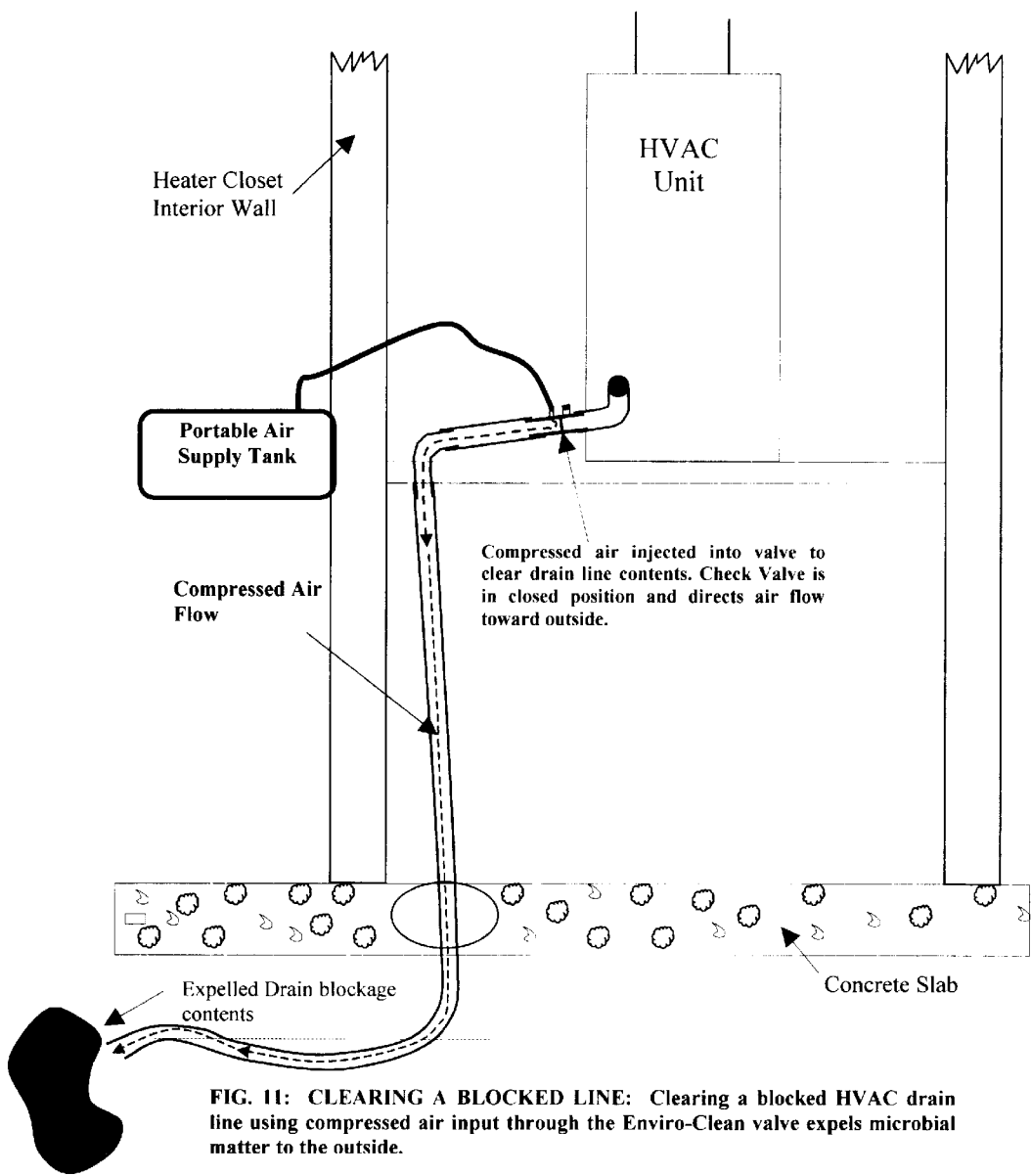
FIG. 11: CLEARING A BLOCKED LINE: Clearing a blocked HVAC drain line using compressed air input through the Enviro-Clean valve expels microbial matter to the outside.
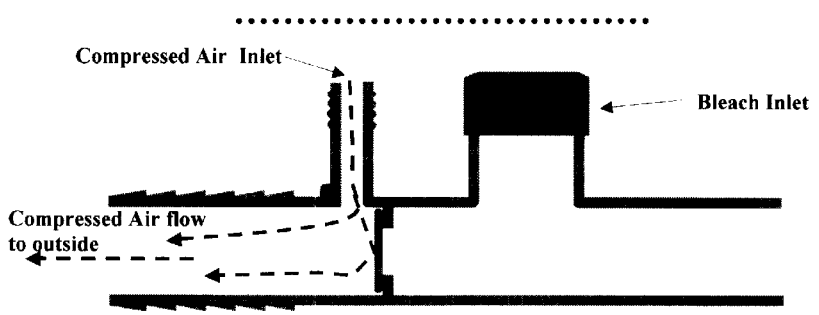
FIG. 12: COMPRESSED AIR FLOW PATTERN: Used to remove drain line blockage.
NOTE: Check valve closure preventing flow into HVAC unit.

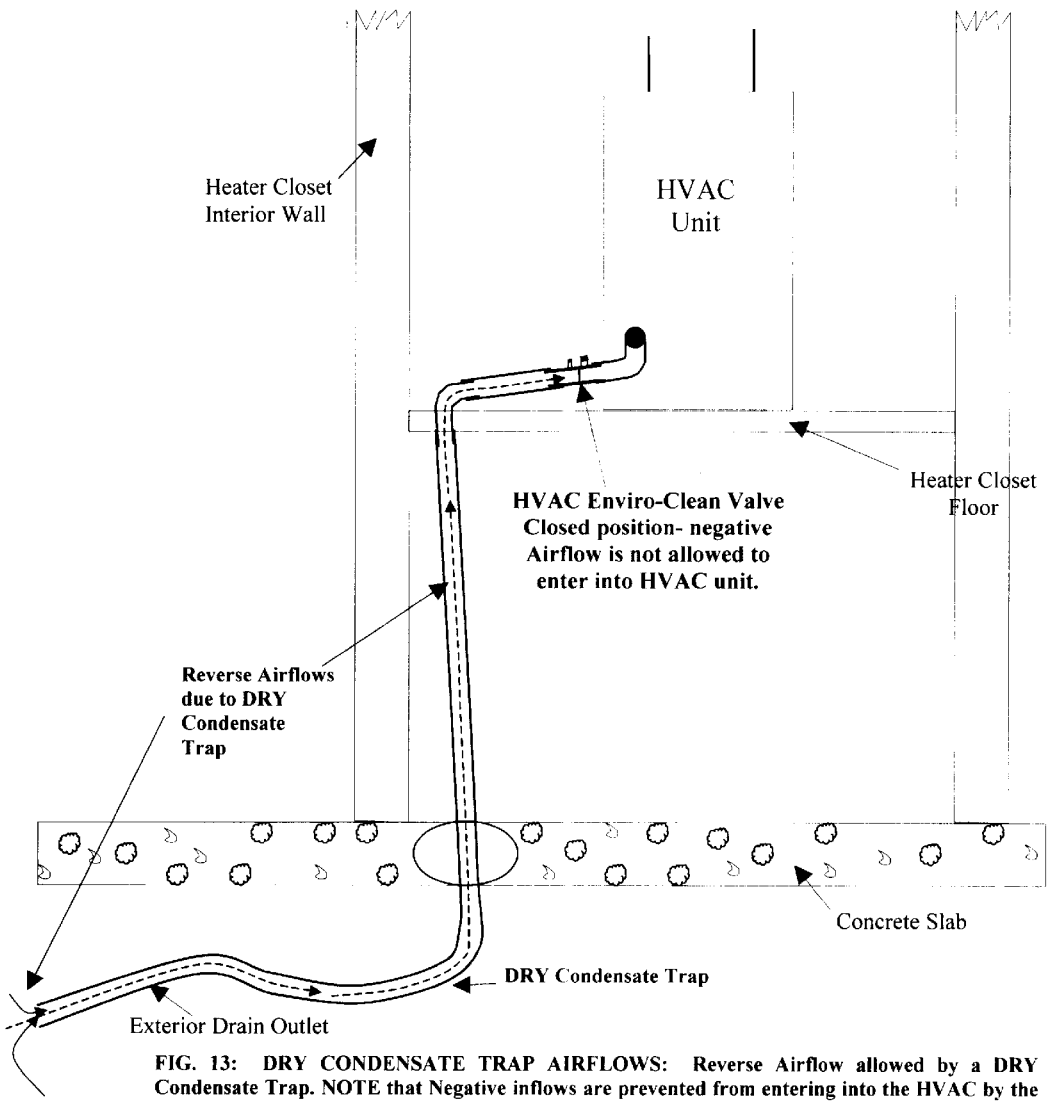

FIG. 13: DRY CONDENSATE TRAP AIRFLOWS: Reverse Airflow allowed by a DRY Condensate Trap. NOTE that Negative inflows are prevented from entering into the HVAC by the closed HVAC Enviro-Clean Valve.

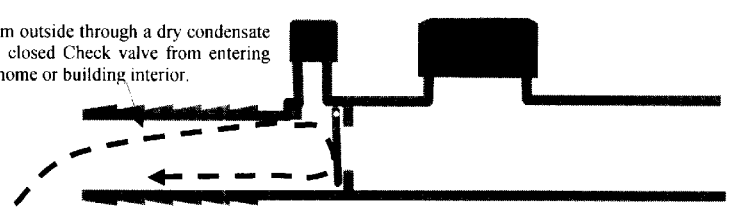

FIG. 14: NEGATIVE AIRFLOW PATTERN THROUGH ENVIRO-CLEAN VALVE: Dry Condensate Trap Reverse Air flow pattern with Enviro-Clean Valve installed in drain line. NOTE: Valve closure preventing undesirable air entry into HVAC unit.

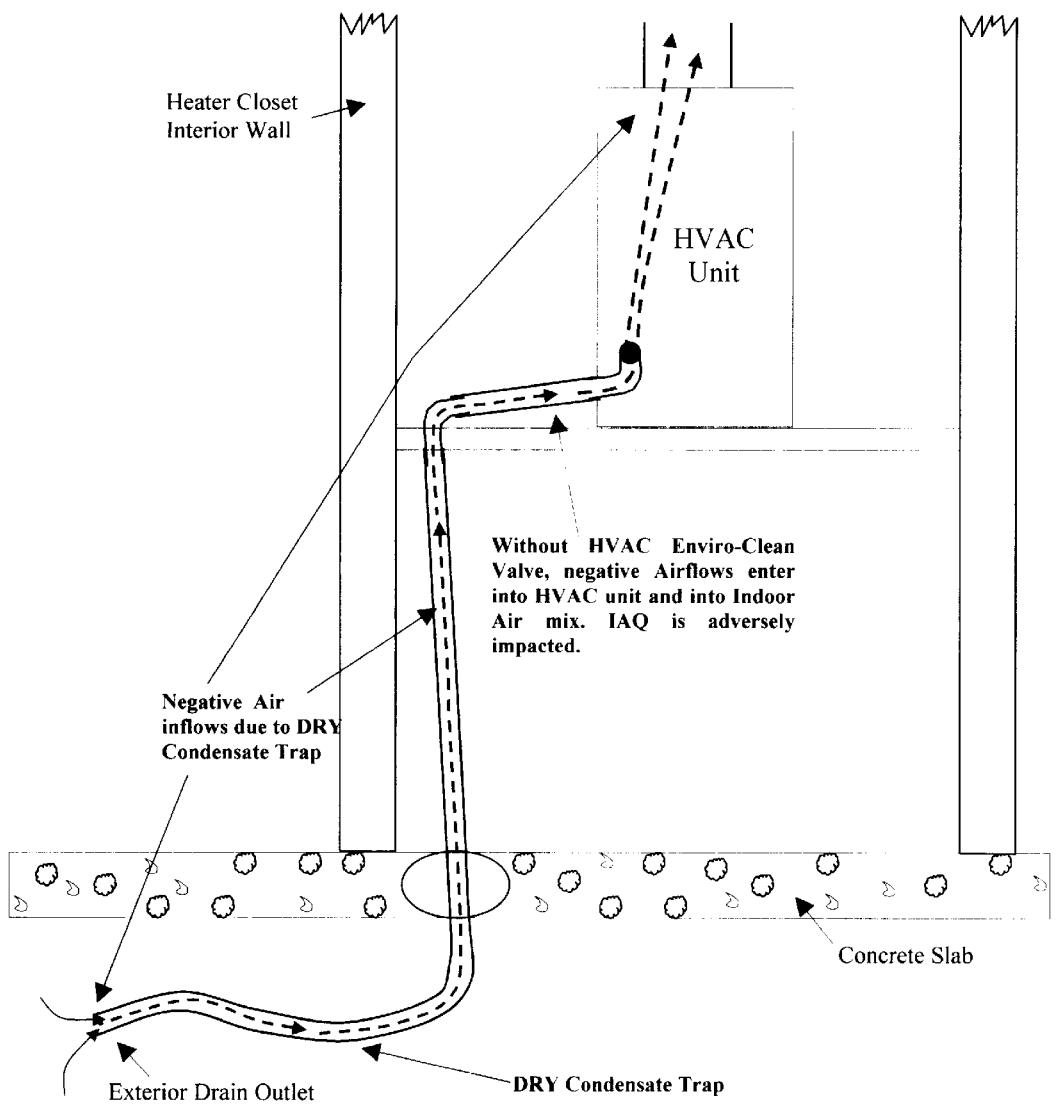
FIG. 15: DRY CONDENSATE TRAP AIRFLOWS WITHOUT ENVIRO-CLEAN VALVE: Without the HVAC Enviro-Clean Valve installed, negative Airflows permitted by a DRY Condensate Trap enter into the HVAC unit and into the interior of residence or building and having a negative affect upon Indoor Air Quality as it becomes part of the indoor air.

HVAC ENVIRO-CLEAN VALVE

BACKGROUND OF THE INVENTION

The field of endeavor to which our invention pertains is Heating, Ventilation and Air Conditioning (HVAC condensate drain lines) for the home, office, and apartment or wherever a heating and cooling air-handling unit may be installed.

Current technology addressing HVAC problems our invention solves is as follows:

1. To disinfect a HVAC condensate drain line, chlorine tablets or other disinfectants are added to the HVAC drain pan by removing the front cover of the HVAC unit and placing the disinfectant into the drain pan. This is very cumbersome and has not been widely accepted by consumers and usually results in discontinued use after a short period of time.
2. When a blockage occurs in a condensate drain line, a HVAC repairman must be called to cut into the line to remove the blockage, which normally results in a costly repair bill to the HVAC user. Another method of cleaning the drain line involves using a water hose to force water into the drain line from the outlet end and many times results in spillage of water, bacteria and microbial matter into the HVAC unit and interior of the building or dwelling, all of which have a negative impact on Indoor Air Quality.
3. There are no known products available that prevents negative airflows into the HVAC unit caused by what is known as the "dry trap syndrome". Our valve design prevents this from occurring and polluted air flowing through a dry condensate drain line from entering into the HVAC unit and the building or home.

BRIEF SUMMARY OF THE INVENTION

One of the most common problems that a user of a Heating, Ventilation and Air Conditioning (HVAC) system faces, is that of clogged condensate drain lines and overflowing drain pans which cause untold damage annually. Typically, when this occurs, the owner or user of the HVAC system must call a repairman to cut the drain line, remove the blockage and clear the line for normal use. This usually occurs numerous times during the life of the HVAC system and results in a costly expense for the consumer for the service call and repair, inconvenience, damage to carpet and building or dwelling interior and a danger to Indoor Air Quality (IAQ).

Current HVAC system installations do not include a method whereby the condensate drain line can be treated to remove microbial and bacterial growth without considerable expense to the consumer.

The instant invention allows for easy access whereby one can easily treat the condensate drain line with inexpensive household bleach to minimize the potential for microbial and bacterial growth while favorably affecting IAQ. If the drain line does become blocked, the line can be cleared by the introduction of compressed air to clear the blockage without the necessity of cutting into the drain line. Additionally, problems associated with a "dry condensate trap" will be eliminated by the prevention of reverse airflows through the drain line. "Dry condensate trap" problems occur during times in which the HVAC unit is sparingly used and the water trap evaporates, thus leaving the drain line open and becomes a source of air intake for the HVAC system and has a detrimental effect on health and IAQ. (See FIGS. 13, 14, & 15)

The primary value of our product to consumers and HVAC system owners is as follows:

1: Economic: Installation can be made during the initial installation of the HVAC unit or a retrofit can be made by the user or owner at anytime and inexpensively. Treatment of the drain line can by made by the consumer cheaply, safely and easily and will eliminate or reduce expensive HVAC service calls. Additionally, the user can open a clogged line using compressed air and without cutting into the drain line.
2: Environmentally safe: Common household bleach can be used to treat a drain line and eliminate most of the microbial and bacterial growth that usually occur in the line without being a detriment to the environment.
3. Indoor Air Quality: By reducing microbial and bacterial growth and reducing drain pan spillages onto carpeting and interior of homes and buildings, there will be an improvement to Indoor Air Quality. Reverse airflows will be eliminated in systems operating with a "dry condensate trap" which will further enhance IAQ.
4. Ease of use and installation: Installation of our valve is easy to perform and can be made in a few minutes with no special tools needed. Once installed, access to the valve unit is easy and the routine treatment procedure of adding bleach to the drain line takes very little time to perform by removing the screw cap, adding a few drops of bleach into the drain line and replacing the cap cover. If a blockage does occur, compressed air can be introduced into the drain line by removing the screw cap on the air injection orifice and placing an air supply hose fitting onto the air inlet. The design of our valve permits the compressed air flow to be directed to the blockage and prevents it from entering into the HVAC unit.

BRIEF DESCRIPTION OF THE SEVERAL VIEWS OF THE DRAWING

1. FIG. 1: HVAC Enviro-Clean Valve—side view
2. FIG. 2: Barb Connection Detail
3. FIG. 3: Compressed Air Inlet Detail
4. FIG. 4: Cross Section at Valve Seat
5. FIG. 5: Cross Section View at Slip Connection End
6. FIG. 6: Cross Section View at Barb Connection End
7. FIG. 7: Normal HVAC Condensate Flow Pattern
8. FIG. 8: Condensate Flow through Enviro-Clean Valve
9. FIG. 9: Disinfectant Input Through Valve
10. FIG. 10: Disinfectant Flow Pattern
11. FIG. 11: Compressed Air Input
12. FIG. 12: Compressed Air Flow Pattern
13. FIG. 13: Dry Condensate Trap
14. FIG. 14: Negative Airflow Pattern with Enviro-Clean Valve installed
15. FIG. 15: Negative Airflow Pattern without Enviro-Clean Valve

DETAILED DESCRIPTION OF THE INVENTION

The instant invention is composed of a Poly Vinyl Chloride (PVC) or equivalent plastic body being 3.75 inches in length, 0.0625 inch wall thickness, an inside diameter of 0.875 inch and an outside diameter of 1 inch on the slip type connection end which allows for a glued connection into a PVC plastic elbow connection at the HVAC unit. Our valve contains an internal wafer check valve designed to prevent inflows into the HVAC unit. The opposite end has an outside diameter of 0.75 inch and an internal diameter of 0.5625 inch and a barbed configuration for attachment to the drain line.(See FIG. 1) Two openings on the top side of the valve body allow the introduction of (1) household bleach measuring 0.75 inch height, 0.25 inch O.D. and 0.125 inch inside diameter, and (2), a compressed air inlet which measures 0.75 inch in height, 0.625 inch O.D. and 0.50 inch inside diameter. The air and bleach openings are covered by screw type plastic caps. (See FIGS. 3, 6, 8, 9, and 11)

The HVAC Enviro-Clean Valve is designed to be installed in-line (See FIG. 7) and allow for easy access by the consumer in a new or existing HVAC condensate drain line to prevent blocking the drain line and minimize the potential for microbial and bacterial growth and a reduction in IAQ pollution. There are a number of potential breeding grounds for bacteria and microbial growth within a HVAC system. Routine maintenance by the HVAC user by adding common household bleach to the drain line through an opening in the valve body will limit the growth of bacteria and microbial matter in the drain line and keep it freely flowing. A second entry point on the valve permits the introduction of compressed air into the drain line (without cutting the line) should the line become clogged, to expel the blockage from the line.

It is desirable to prevent HVAC drain pans from overflowing and causing interior damage to homes and other buildings. Odors caused from damaged carpets which can remain wet for extended period of time and be a source of microbial and bacterial growth and cause a reduction in IAQ and unhealthy to the user. It is desirable to prevent air inflows into the HVAC system as a result of a "dry condensate trap". The HVAC Enviro-Clean Valve is designed to prevent reverse airflows into the HVAC system through a dry condensate drain line. (See FIG. 13, 14, 15)

What is claimed is:

1. A plastic flow control device attached to a HVAC unit and connected to a condensate drain line for sanitizing the condensate line and removal of blockages within the drain line by the introduction of compressed air into the line, and is comprised of an inlet port of the flow control device having one end connected to a condensate outlet port of the HVAC unit;

an outlet port of the flow control device having the other end connected to an upstream end of the condensate line;

a cleaning port of the flow control device, adapted to allow the introduction of a cleaning fluid for sanitizing and removal of any blockages or microbial growth within the condensate line, a flushing port of the flow control device, adapted to allow an outside compressed air source to be introduced, for the purpose of flushing any blockages or microbial growth within the condensate line; and a single internal check valve disposed between the cleaning port and the flushing port within the flow control device for the purpose of directing compressed air flow therein and simultaneously preventing reverse compressed air and reverse fluid flow into the HVAC unit, whereby during normal operation the check valve is allowed to open freely when fluid flows from the HVAC unit and/or when the cleaning fluid is added through the cleaning port to the condensate line.

2. The flow control device of claim 1, wherein the check valve remains open during normal operation and moves to a closed position without manual intervention upon the introduction of compressed air into the flushing port for the purpose of removing any blockages within the condensate line.

3. The flow control device of claim 1, wherein the check valve remains open during periods of normal operation and allows the check valve to move to a closed position without manual intervention in the event of a dry condensate line, thus reducing or preventing air inflows across residual microbial growth within the condensate line and into dwelling or office airspace.

* * * * *